United States Patent
Fenton, Jr. et al.

[11] Patent Number: 5,964,765
[45] Date of Patent: Oct. 12, 1999

[54] SOFT TISSUE FIXATION DEVICE

[75] Inventors: Paul V. Fenton, Jr.; Thomas D. Egan, both of Marblehead; Richard B. Streeter, Andover, all of Mass.

[73] Assignee: Axya Medical, Inc., Beverly, Mass.

[21] Appl. No.: 09/061,608

[22] Filed: Apr. 16, 1998

[51] Int. Cl.[6] .................................................. A61B 17/56
[52] U.S. Cl. .............................. 606/72; 606/74; 606/61; 606/60; 606/103; 606/232
[58] Field of Search ................................ 606/74, 61, 72, 606/60, 103, 232

[56] References Cited

U.S. PATENT DOCUMENTS

| | | | |
|---|---|---|---|
| 5,356,412 | 10/1994 | Golds et al. | 606/74 |
| 5,356,417 | 10/1994 | Golds | 606/151 |
| 5,383,905 | 1/1995 | Golds et al. | 606/232 |
| 5,413,585 | 5/1995 | Pagedas . | |
| 5,437,685 | 8/1995 | Blasnik | 606/151 |
| 5,500,018 | 3/1996 | Spotorno et al. | 623/11 |
| 5,611,801 | 3/1997 | Songer | 606/73 |
| 5,766,218 | 6/1998 | Arnott | 606/151 |

*Primary Examiner*—Michael Buiz
*Assistant Examiner*—Tan-Uyen T. Ho
*Attorney, Agent, or Firm*—Lappin & Kusmer LLP

[57] ABSTRACT

A single-piece soft tissue fixation device includes an elongated element terminating in a tip at one end and a receptacle at the other end which bond with each other in a welded joint. The device is made of a heat-bondable, biocompatible material that can be ultrasonically or thermally welded. The tip and receptacle of the device can be textured or contoured or otherwise complementarily configured to promote mutual engagement prior to and during bonding. The tip can include a needle or needle-like extension for penetrating tissue. The device may be at least partially resorbable in living tissue.

9 Claims, 3 Drawing Sheets

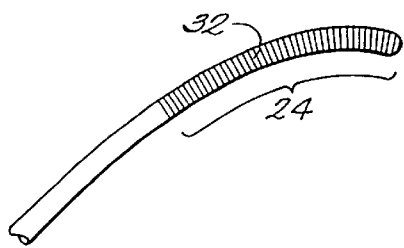
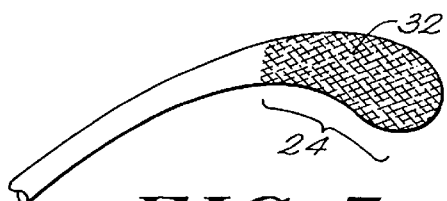
*FIG. 6*  *FIG. 7*
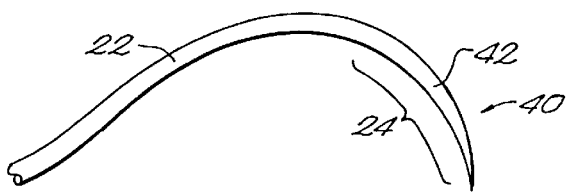
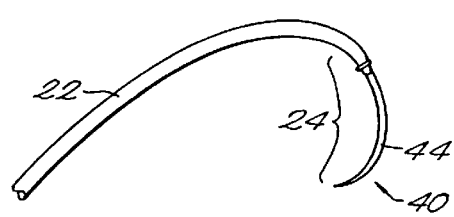
*FIG. 8*  *FIG. 9*
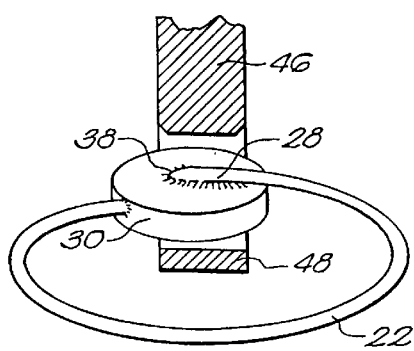
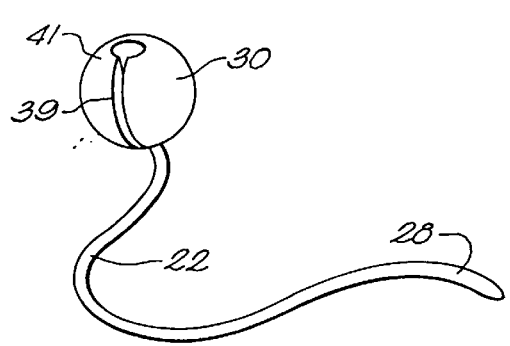
*FIG. 10*  *FIG. 11*

SOFT TISSUE FIXATION DEVICE

FIELD OF THE INVENTION

The invention is related to surgical fixation devices for fixing soft tissue to bone, and in particular to fusible, one-piece soft tissue fixation devices.

BACKGROUND OF THE INVENTION

In the surgical repair of soft tissue, such as, for example, the surgical reattachment of a torn ligament to bone, it is known to use multi-part devices to fix the soft tissue to the bone. The multi-part devices typically include a screw or other bone anchoring device, and a button-like device for anchoring the suture therein. The anchor is installed in a predrilled hole in the bone, and the soft tissue is fixed to the anchor in the bone with sutures, which are fastened together with the button instead of with knots.

A disadvantage of such devices is that the quality and strength of the device may be limited by the quality and strength of the suture, and/or by the integrity of the attachment of the device to the bone. The soft tissue will detach from the anchor in the bone if the suture slips or breaks. If the anchor or the button slips or becomes dislodged, the soft tissue will not remain anchored to the bone.

Another disadvantage of such a device is its multi-part nature. It is difficult to join the button and the anchor with a suture and maintain the button appropriately oriented with respect to the anchor and to the tissue while the suture is appropriately tensioned and fastened in situ.

U.S. Pat. No. 5,413,585 to Pagedas discloses a self-locking suture which includes a suture lock crimped onto a suture thread. The suture lock admits a suture in one direction only and does not permit withdrawal of the suture from it. No knots are required in the suture, as it forms a locked stitch. In addition, the suture can be tensioned and the locked stitch formed by a single pair of hands in a simplified operation.

The Pagedas self-locking suture relies on a mechanical locking device to form the locked stitch. It is therefore relatively complex and is subject to breakage and slippage.

It would be an advantage to provide a surgical soft tissue fixation device which overcomes the disadvantages of the prior art devices.

SUMMARY OF THE INVENTION

The present invention provides a single-piece soft tissue fixation device which can be bonded in situ upon the application of ultrasonic or thermal energy to it so as to attach soft tissue to bone or to other soft tissue.

According to one aspect of the invention, the fixation device comprises an elongated flexible element extending between opposed first and second ends, the first end including a fusible tip and the second end including a fusible receptacle. The tip and the receptacle are adapted for bonded engagement with each other upon the application of energy to at least one of them.

In one embodiment, at least the tip and receptacle of the device are made of a polymeric material which can be welded upon application of ultrasonic or thermal energy thereto. The surfaces of the tip and receptacle may optionally be textured to promote their mutual engagement. The receptacle may be contoured to retain and engage the tip. In a preferred embodiment, the receptacle may include a wedge element to retain and engage the tip therein.

In one embodiment, the tip may include means, such as a needle or a needle-like extension of the elongated element, for penetrating living tissue. In another embodiment, at least the elongated element may be made of a biocompatible, resorbable material.

These and other features of the invention will be more fully appreciated with reference to the following detailed description which is to be read in conjunction with the attached drawings.

BRIEF DESCRIPTION OF THE DRAWINGS

The invention is further described by the following description and figures, in which:

FIG. 6 is a detail view of one embodiment of the tip, which is scored;

FIG. 7 is a detail view of another embodiment of the tip, which is scored and relatively large in area;

FIG. 8 is a detail view of an alternative embodiment of the tip which includes a needle-like extension;

FIG. 9 is a detail view of still another embodiment of the tip which includes an attached surgical needle;

FIG. 10 is a perspective view of a fixation device being fused at the tip and receptacle by the application of energy, such as from an ultrasonic welding horn or from a heat source;

FIG. 11 is a perspective view of an alternate embodiment of fixation device, which includes a contoured receptacle with a wedged opening or slit to receive the tip;

Like elements in the respective FIGURES have the same reference numbers.

DETAILED DESCRIPTION OF THE PREFERRED EMBODIMENT

Figure 1:
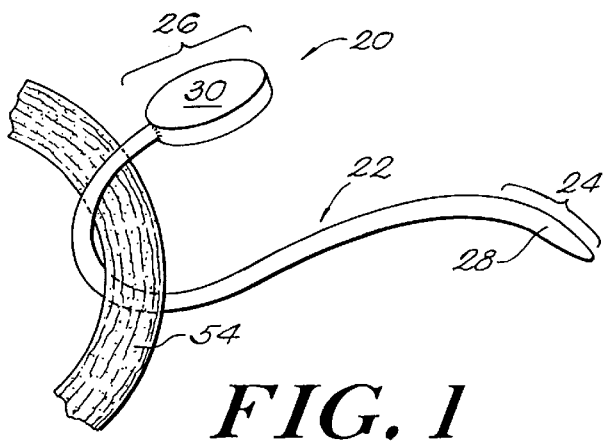
FIG. 1 is a perspective view of a fixation device according to the invention.

The soft tissue fixation device 20 of the present invention is illustrated generally in FIGS. 1, 2, 10, 11, 12, 13 and 14. The device is in the form of an elongated element 22 which extends between opposed first and second ends 24, 26. The first end 24 includes a fusible tip 28, and the second end 26 includes a fusible receptacle 30. The tip and receptacle are adapted for bonded engagement with each other upon the application of energy, such as thermal or ultrasonic energy, as illustrated in FIG. 10, to at least one of the tip and the receptacle, as detailed below.

At least the tip and the receptacle of the device are preferably made of a polymeric material which can be bonded or welded with the application of heat. The elongated element 22 may also be made of a bondable polymeric material.

Figure 3A:
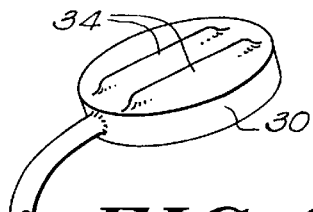
FIG. 3A is a perspective view of one embodiment of the receptacle of the fixation device.
Figure 3B:
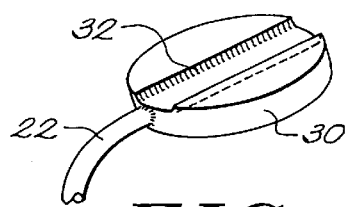
FIG. 3B is a perspective view of another embodiment of the receptacle.
Figure 4:
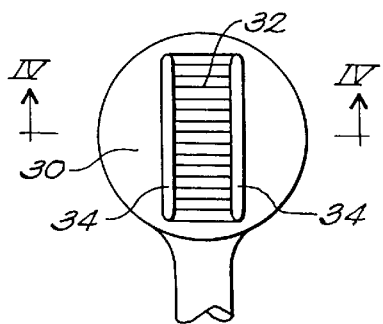
FIG. 4 is a plan view of another embodiment of the receptacle.
Figure 5:
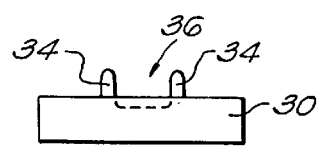
FIG. 5 is a section view of the receptacle of the device of FIG. 4, taken along section lines IV—IV.

As shown in FIGS. 3B, 4, 6, 7, 13 and 14 the exterior surfaces of at least one of the tip and the receptacle may include textured portions 32, such as a knurled, scored or serrated region, to promote frictional retention and engagement of the tip and receptacle prior to and during the bonding process. The receptacle 30 may be in form of a pair of raised ridges 34 which form a channel 36 that approximates the width of the tip portion, as shown in FIG. 3A, 4 and 5, so as to capture and retain the tip prior to and during bonding. Alternatively, the receptacle 30 may include a slot 35, as shown in FIG. 3B, with serrations 32 on the vertical side surfaces of the slot, to promote retention and engagement with the tip, which may be correspondingly textured. Insertion of the tip 28 into the slot 35 can be done incrementally by sliding the tip 28 axially into the slot from the end closest to the elongated element 22, or by placing the tip directly into the slot from above. Such placement allows the device to have a variable size for optimum versatility in use, while the serrations on the vertical or bottom surfaces of the slot retain the tip in the slot to achieve the desired tensioning of the device prior to and during bonding.

Figure 12:
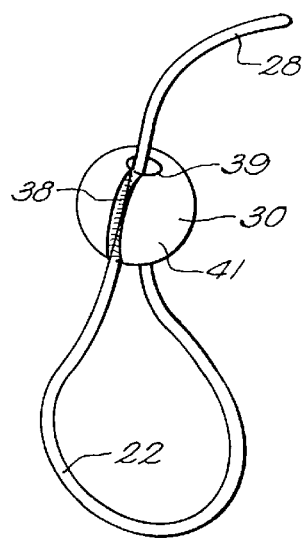
FIG. 12 is a perspective view of the device of FIG. 11 showing engagement of the tip in the receptacle.
Figure 13:
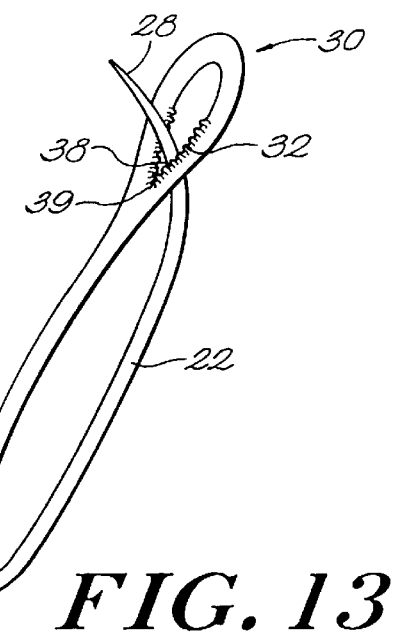
FIG. 13 is a perspective view of another embodiment of the device, which includes a receptacle having an eyelet with a partially textured contact surface to receive and engage the tip.
Figure 14:
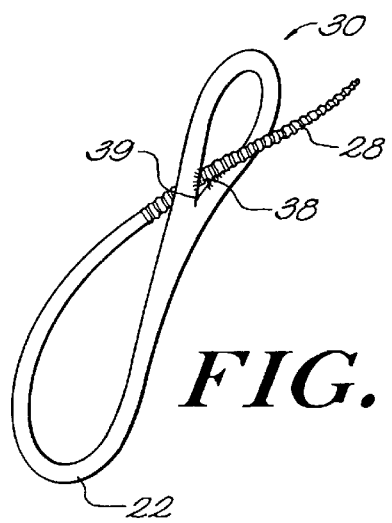
FIG. 14 is a perspective view of another embodiment of the device shown in FIG. 13, in which the tip is textured to promote retention and engagement in the eyelet.

The weld region 38 of the tip and receptacle, shown most clearly in FIGS. 2, 10, 12, 13 and 14, is preferably relatively large in area so as to provide high bond strength and shear resistance. The enlarged tip 32 in FIG. 7 enhances bond strength by providing a relatively large bonding area, particularly in the absence of other surface features. A relatively long weld area 38 is shown in the embodiment of FIG. 12, which includes a spherical receptacle 41 with a slit or wedge element 39 into which the tip can be inserted and retained. The embodiments of FIGS. 13 and 14 also have relatively large bond areas as a result of the relatively large contact surface areas of the tip and eyelet, which include a wedge portion 39, into which the tip can be inserted and retained.

As shown in FIGS. 8 and 9, the tip 28 can include a penetrating end 40 which is adapted to penetrate soft or bony living tissue. In one embodiment, the penetrating end 40 can be a hardened, needle-like extension 42 of the elongated element which can penetrate soft tissue or other relatively soft materials. In another embodiment, the penetrating end 40 can be a surgical needle 44, as shown in FIG. 9, which is attached to the tip of the device, such as by welding or other known joining processes. Depending on the intended application for the device, it may be necessary or desirable to drill holes in bone or other relatively hard or dense tissue to facilitate passage of the tip of the device therethrough.

In a preferred embodiment, at least the elongated element 22 is made of a resorbable, biocompatible material which can be resorbed into living tissue after its tissue-holding capability is no longer required. Because the elongated element 22 has a relatively small cross-section, it is likely to be resorbed into living tissue faster than the bonded tip and receptacle. Resorption rate can thus be controlled by controlling the dimensions of the various components of the device.

Figure 2:
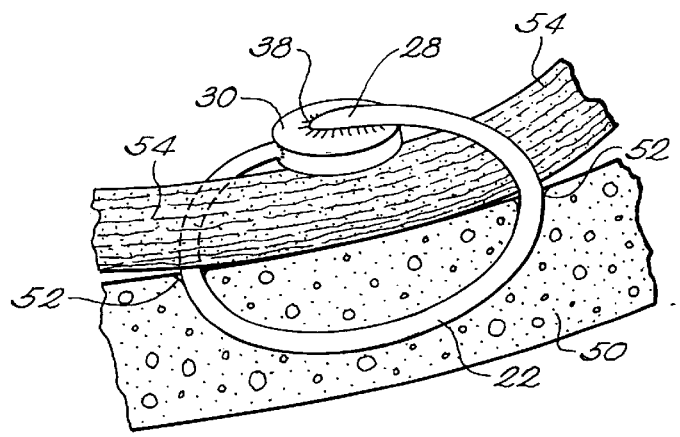
FIG. 2 is a perspective view of a fixation device in use.
Figure 15:
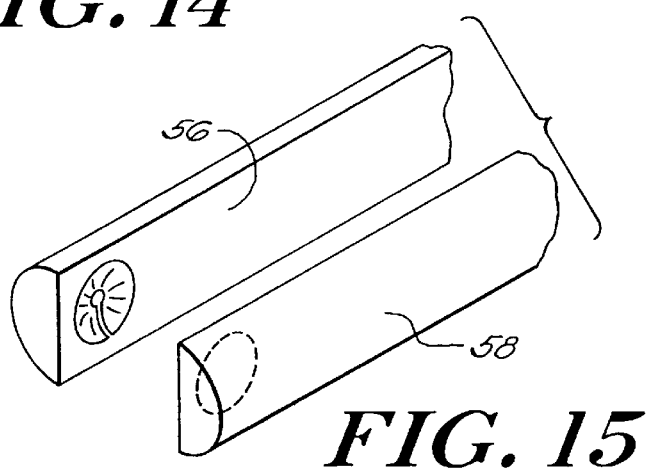
FIG. 15 is a perspective view of an ultrasonic weld horn and anvil useful in bonding the device shown in FIGS. 11 and 12.

As shown in FIG. 10, an ultrasonic welding horn 46 can be applied to the tip and receptacle 28, 30 while they are engaged. If the application permits, a stationary anvil 48 can be placed beneath the tip and receptacle to compress them together in the ultrasonic welding apparatus. Otherwise, as shown in FIG. 2, a bone 50 through which the device is threaded can act as the stationary anvil. Ultrasonic energy is transmitted from one or more piezoelectric transducers (not shown) into the horn 46 and to the tip 28 of the device, which vibrates relative to the stationary receptacle 30 abutting the stationary anvil. The relative motion of the tip and receptacle establishes frictional heating at the interface between them and causes localized melting of the tip and receptacle at that interface. Pressure applied to the tip and receptacle during melting causes them to fuse together. This occurs in each of the three embodiments shown in FIGS. 1, 11 and 13. The embodiment of FIG. 11, which includes a spherical receptacle 41, preferably is bonded by application of a correspondingly-shaped ultrasonic weld horn 56 and anvil 58, shown in FIG. 15.

Alternatively, the ultrasonic welding apparatus can be replaced with a heated probe or other source for transmitting thermal energy directly into the tip and receptacle to melt and bond them together.

It should be noted that the tip 28 of the device may extend for some length along the elongated element 22 and may therefore be bonded to the receptacle at any location along the elongated element other than at its extreme end, as shown, for example, in FIG. 12. Any portion of the elongated element 22 may be bonded to the receptacle 30, provided it is made of a bondable material.

The device in use is illustrated in FIG. 2. A bone or other living tissue 50 may have a pair of holes 52 drilled into it to intersect so as to create a passage for the fixation device. A segment of soft tissue 54 is captured by the loop formed by the device and held fast to the bone 50 as the tip 28 engages with the receptacle 30 in preparation for bonding. Application of energy to the tip and receptacle of the device causes them to bond together as a result of localized melting, thus creating a fused loop to hold the soft tissue to the bone.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

I claim:

1. A one-piece fixation device for attachment of soft tissue to bone, comprising an elongated flexible element extending between opposed first and second ends, the first end including a fusible tip and the second end including a fusible receptacle, wherein the tip and the receptacle are adapted for fused engagement with each other upon the application of energy to at least one of the tip and the receptacle when the tip and receptacle are in physical contact with each other.

2. A fixation device according to claim 1, wherein at least the tip and the receptacle of the device are made of a polymeric material which can be fused together upon application of ultrasonic or thermal energy thereto.

3. A fixation device according to claim 2, wherein at least a portion of the surfaces of at least one of the tip and the receptacle are textured to promote mutual engagement of the tip and receptacle.

4. A fixation device according to claim 3, wherein the receptacle is contoured to retain and engage the tip therein.

5. A fixation device according to claim 4, wherein the receptacle includes a wedge element for engaging and retaining the tip.

6. A fixation device according to claim 4, wherein the tip includes means for penetrating living tissue.

7. A fixation device according to claim 6, wherein the means for penetrating living tissue comprises a needle attached to the elongated element.

8. A fixation device according to claim 6, wherein the means for penetrating living tissue comprises a hardened needle-shaped end extending from the tip of the elongated element.

9. A fixation device according to claim 4, wherein at least the elongated element is made of a biocompatible, resorbable material.

\* \* \* \* \*